United States Patent [19]

Harris, Jr. et al.

[11] 4,289,912
[45] Sep. 15, 1981

[54] STABILIZATION OF LIQUID PARAFORMALDEHYDE

[75] Inventors: Marvin E. Harris, Jr.; Hubert H. Thigpen, both of Corpus Christi, Tex.

[73] Assignee: Celanese Corporation, New York, N.Y.

[21] Appl. No.: 146,945

[22] Filed: May 2, 1980

[51] Int. Cl.$^3$ ............................................. C07C 47/04
[52] U.S. Cl. ..................................... 568/422; 568/421
[58] Field of Search ................................ 568/422, 421

[56] References Cited

U.S. PATENT DOCUMENTS

| | | | |
|---|---|---|---|
| 2,000,152 | 5/1935 | Walher | 568/422 |
| 2,492,453 | 12/1949 | Yates | 568/422 |
| 2,568,016 | 9/1951 | MacLean | 568/422 |
| 2,568,017 | 9/1951 | MacLean | 568/422 |
| 3,137,736 | 6/1964 | Prinz et al. | 568/422 |
| 3,287,414 | 11/1966 | Fukui et al. | 568/422 |
| 3,359,326 | 12/1967 | Locke | 568/422 |
| 3,379,769 | 4/1968 | Prinz et al. | 568/422 |
| 3,532,756 | 10/1970 | Prinz et al. | 568/422 |
| 3,745,190 | 7/1973 | Prinz et al. | 568/422 |
| 3,781,365 | 12/1973 | Prinz et al. | 568/422 |
| 3,816,539 | 7/1974 | Sanborn et al. | 568/422 |

FOREIGN PATENT DOCUMENTS

| | | | |
|---|---|---|---|
| 686830 | 5/1964 | Canada | 568/422 |
| 41-3734 | 3/1966 | Japan | 568/421 |

*Primary Examiner*—Werren B. Lone
*Attorney, Agent, or Firm*—Ralph M. Pritchett

[57] ABSTRACT

The tendency of liquid paraformaldehyde containing water and paraformaldehyde in, for example, approximately 80% to approximately 90% concentration to precipitate solid paraformaldehyde therefrom is retarded by the incorporation thereinto of an effective amount of a moderator or stabilizer selected from the group consisting of polyacrylic acid, tartaric acid, dl-malic acid, ethylenediaminetetraacetic acid, and citric acid. The prior-art stabilizers known and used for lower-concentration formaldehyde solutions of, for example, about 50% strength are not effective. Conversely, the present moderators are not effective in the lower-concentration solutions.

5 Claims, No Drawings

STABILIZATION OF LIQUID PARAFORMALDEHYDE

BACKGROUND OF THE INVENTION

This invention relates to the manufacture and processing of liquid paraformaldehyde, by which is meant liquid mixtures consisting essentially of water and paraformaldehyde with the paraformaldehyde being present in concentrations ranging from approximately 70% up to about 91% by weight. More particularly, the invention is directed especially to the manufacture and handling of liquid paraformaldehyde containing approximately 80% to approximately 89% paraformaldehyde.

Liquid paraformaldehyde has two major industrial uses. First, it is an intermediate in preparing the relatively water-free hemiformal compositions which are available from, for example, the Celanese Chemical Company under the tradename "Formcel". Second, liquid paraformaldehyde is an intermediate in the manufacture of solid flake or powder paraformaldehyde, which is prepared by concentrating aqueous formaldehyde solutions by vacuum evaporation followed by cooling and flaking the resulting concentrate. The flake product can be subsequently ground to a powder if desired. The manufacture of flake paraformaldehyde in this manner, including the step of concentrating a relatively dilute formaldehyde solution to the liquid paraformaldehyde product with which the U.S. Pat. Nos. 2,568,016 and 2,568,017 to MacLean and Heinz, assigned to Celanese Corporation of America. The heart of the process as described in these patents is the vacuum evaporation of, for example, 40% to 50% aqueous formaldehyde under controlled conditions of temperature, pressure, pH and liquid retention time in a two-stage vacuum evaporation system. Liquid paraformaldehyde as contemplated by the present invention can be drawn from either of the two evaporation stages, the liquid drawn from the first evaporation stage being, of course, more dilute than that from the second stage.

The details of the prior-art concentration process just summarized above are not relevant to the present invention except that, regardless of whichever of the myriad possible modifications of this evaporation process one might happen to be employing, it will be characterized by the presence of concentrated liquid paraformaldehyde which, in turn, will be in contact with the interior surfaces of the processing equipment including vessels, piping, and, of particular importance in the present context, heat exchangers.

The present invention is directed to a processing problem which has been found to affect all process apparatus containing concentrated liquid paraformaldehyde but especially heat exchangers, such as the heating elements of the evaporators which are used in evaporating formaldehyde to produce the concentrate. Briefly, this problem is that liquid paraformaldehyde, especially when it is being heated, tends to deposit solid paraformaldehyde of high molecular weight, with resulting fouling of the surfaces of the process equipment, especially heat exchangers, such that it becomes necessary to interrupt operations for the purpose of removing these deposits. These interruptions in the manufacturing process are, of course, costly and troublesome.

It might be expected from the existing prior art that the apparatus fouling problem could be alleviated by incorporating into the paraformaldehyde solutions which are being processed any of a large number of stabilizers which are known to be effective in maintaining the clarity of those aqueous solutions containing 50% or so of formaldehyde which are the usual form in which formaldehyde is stored and transported. (It will be understood that the concentrated paraformaldehyde solutions to which the present invention is directed are normally used quickly at or near the site where they are produced. They are not stored for any length of time nor are they shipped for any great distance.) The prior-art formaldehyde stabilizers are, broadly, organic colloids ranging from naturally-occurring gums to synthetic high-molecular weight materials such as cellulose esters and polyvinyl alcohol. The prior art as related to known stabilizers for aqueous formaldehyde solutions is exemplified by U.S. Pat. Nos. 3,137,736; 3,379,769; 3,532,756; 3,745,190; 3,781,365; and 3,816,539.

Surprisingly, however, it has been discovered that incorporating stabilizers of the type taught in the prior art, which are generally organic colloids or in any event molecules of high molecular weight, has no significant effect in alleviating the problems discussed hereinabove which are encountered in processing liquid paraformaldehyde. Thus, the known prior art affords no assistance in coping with the problem, and those engaged in manufacturing and/or handling concentrated liquid paraformaldehyde have continued to seek a method for alleviating the problem of apparatus fouling and the resultant interruptions in plant operation which stem from it.

It is an object of the present invention to provide a method for retarding the deposition of solid paraformaldehyde from liquid paraformaldehyde compositions. It is another object to provide a method for extending the onstream time of apparatus which is employed in manufacturing and/or utilizing liquid paraformaldehyde. It is another object to provide new compositions of matter, in the form of concentrated liquid paraformaldehydes which have a reduced tendency to deposit solid paraformaldehyde on the interior surfaces of process apparatus within which they are contained. Other objects will be apparent from the following detailed description and claims.

SUMMARY OF THE INVENTION

In accordance with the present invention the troublesome tendency of liquid paraformaldehyde, especially that containing at least about 75% paraformaldehyde and more typically that containing at least about 80% paraformaldehyde, to form deposits of solid paraformaldehyde on the interior surfaces of apparatus in which it is contained or in which it is being processed is alleviated by incorporating thereinto an effective amount of a moderator or stabilizer which is a member of the group consisting of polyacrylic acid, tartaric acid, dl-malic acid, ethylenediaminetetraacetic acid, and citric acid. By an "effective amount" is meant a concentration of said moderator which is either sufficient to bring about a reduction in apparatus fouling as determined by operating experience or else an amount which is sufficient to bring about a perceptible increase in "cloud time", which will be explained hereinbelow and which serves as an index of the tendency of a given sample of liquid paraformaldehyde to form solid precipitates. Typically the moderators are effective in a concentration range of about 10 ppm to 50 ppm, although it will be understood that the invention lies primarily in the discovery of the identity of the moderators as distinguished from their effective levels, which in a given instance can readily be determined experimentally as will be explained.

DETAILED DESCRIPTION OF THE INVENTION

It is to be understood that this invention is not directed to the long-term stabilization of solutions of formaldehyde or paraformaldehyde in the manner characteristic of the prior-art stabilizers which are used with aqueous formaldehyde of, say, 50% concentration. That is, the avoidance of solids precipitation over time periods measured in days or weeks is not contemplated. Rather, what is sought and accomplished herein is the prevention of the rapid formation of paraformaldehyde deposits which comprise unusually long-chain polymers and which are therefore unusually troublesome in apparatus in which paraformaldehyde is being manufactured or otherwise handled. In other words, the effect is one of retarding or moderating precipitation of solid paraformaldehyde rather than preventing it altogether. For example, when liquid paraformaldehyde is to be chilled and flaked into solid flake paraformaldehyde it is desired that it solidify at the proper stage in the process (i.e., when it is chilled and flaked). Thus, the compounds the use of which is central to the present invention might better be spoken of as polymerization moderators or retarders rather than as stabilizers in the usual sense of the term as used in the formaldehyde art. It is believed, in fact, that the mechanism by which the present stabilizers, retarders, or moderators act is different from the stabilizing mechanisms through which the usual prior-art formaldehyde stabilizers maintain clarity in aqueous formaldehyde of, for example, 50% concentration. For example, methyl cellulose, which is typical of the usual formalin stabilizers, is not effective.

It is believed that the problem of apparatus fouling due to high molecular weight paraformaldehyde polymers may be related to the presence of trace contamination by such metals as iron, which are present even in apparatus manufactured from corrosion-resistant alloys such as stainless steel. Accordingly, there would seem reason to believe that, if this is indeed the case, the admixture of any chelating agent into the formaldehyde might reduce the undesired catalytic effect of such trace metal contaminants. It is believed that the action of the stabilizers or moderators of the present invention does involve some sort of chelation mechanism. However, it has also been found that not all chelating agents are effective so that, therefore, it over-simplifies the problem and the related solution to view the paraformaldehyde precipitation as being caused by trace metal contaminants and the solution to the problem to be simply the addition of a chelating agent. For example, tetrasodium ethylenediaminetetraacetic acid, a known chelating agent, has been found to be ineffective for the present purpose. Thus, although the compounds which have been found effective can all be characterized as having a chelating action, and although an additional characteristic which they have in common is that they are all multifunctional carboxylic acids or hydroxy acids, it has not been found possible to characterize the effective compounds broadly. Although with the guidance of the present disclosure it may be possible to identify suitable compounds which have not yet been tested, the only compounds which have been found effective for the present purpose are: polyacrylic acid, tartaric acid, dl-malic acid, ethylenediaminetetraacetic acid, and citric acid. In the case of the polyacrylic acid, molecular weight has not been found to be a critical parameter, but the polyacrylic acid which has been tested and found to be specifically effective has a molecular weight of about 70,000 to 110,000 (average 90,000). Of these effective compounds, citric acid in particular has been found to be reliable and easy to use.

Aqueous formaldehyde solutions containing the present stabilizer-moderators are themselves new compositions of matter having unexpected properties in that, when they are concentrated to a paraformaldehyde level of about 75% to 80% or higher, they display the reduced tendency to deposit high molecular weight solid paraformaldehyde as previously explained. Below about 75% to 80% paraformaldehyde content, usually below about 80%, the action of the stabilizers as indicated by "cloud time" is not noticeable although, of course, as the concentration is reduced the problem of the paraformaldehyde deposits is also readily less important. In any case, to repeat the point, even in those compositions containing formaldehyde and the present stabilizers in relatively dilute aqueous solutions below, for example, about 80%, the inherent advantage still exists in that, in any subsequent processing in which the material is concentrated to, for example, about 80%, the protective effect of the present additives will manifest itself in the form of a reduced tendency to deposit long-chain solid paraformaldehyde. It will also be understood that, in addition to the reduction in tendency toward paraformaldehyde deposition, the present additives, by what is believed to be a chelation effect, can retard or prevent any of several deleterious effects which result from the presence of, for example, trace quantities of iron when the liquid paraformaldehyde containing the additives is used subsequently in any of a number of applications as a chemical intermediate.

In incorporating the present stabilizer-moderators into aqueous formaldehyde or paraformaldehyde, it is not necessary to use any specialized method. The stabilizers are water soluble or water-dispersible, and can be incorporated into the aqueous formaldehyde or paraformaldehyde by the obvious methods of injecting them in water solution into an agitated tank containing the liquid which is to be stabilized or, alternatively, continuously introducing an aqueous solution of the stabilizer at a controlled rate into a pipe through which is flowing the liquid which is to be stabilized. In the case of paraformaldehyde production according to the process described in the MacLean et al. patents previously referred to, it is convenient to incorporate the stabilizer into the relatively dilute (i.e., about 50%) formaldehyde solution before it is introduced into the evaporator system to be concentrated. Being of very low volatility, the stabilizer is concentrated in the evaporation system and remains with the concentrated paraformaldehyde product. The rate at which the stabilizer is admixed into the formaldehyde can be determined on the basis of plant operating experience, that is, gradually increasing the rate over a period of, say, weeks, until the desired reduction in rate of apparatus fouling has been attained. Satisfactory results in a typical paraformaldehyde manufacturing process have been obtained when citric acid was incorporated into the dilute formaldehyde feedstock at a level of about 25 ppm, the citric acid being introduced as a 50% solution in water. Under such conditions the final concentration of the citric acid in the final paraformaldehyde concentrate drawn from the residue of the second paraformaldehyde evaporator would be about 20 to 25 ppm. Alternatively, it is possible, if desired, to introduce the stabilizer directly into either of the evaporation stages but especially into the second stage where the problem of apparatus fouling is most serious.

If it is not desired to use the essentially cut-and-try method of determining optimum stabilizer addition rate as described above, it is possible to use a "cloud time" test to determine the level at which a stabilizer should be used in a given liquid paraformaldehyde. For example, to test the effectiveness of a given stabilizer in paraformaldehyde production, and also to determine the level which is necessary for efficacy, the procedure is as follows:

1. The stabilizer to be tested is admixed into about 1300 ml of an approximately 51% concentration solution of formaldehyde at about 65° C. A stabilizer concentration of about 10 to 50 ppm is suitable for an initial screening level or to compare one additive against another.

2. The solution as prepared above is then concentrated by evaporation under about 200 to 220 mm mercury absolute pressure to a formaldehyde concentration of about 86 to 88% (which corresponds approximately to the highest concentration attained in paraformaldehyde manufacture). Advantageously the evaporation is conducted in an electrically-heated thermo siphon glass laboratory reboiler.

3. The liquid paraformaldehyde concentrate from the preceding step is then transferred to a glass bottle, conveniently of about 2 ounce capacity, the bottle then being capped and suspended in an oil bath maintained at 100° C.

4. The time interval between the time of immersion of the glass bottle in the oil bath to the time when a thermometer bulb cannot be seen behind the bottle (because of haze formation in the liquid paraformaldehyde) is the cloud time. It will be seen, of course, that the initial concentration of stabilizer in the material which is evaporated in step 2 can be varied as desired, and that the weight of evaporator distillate and evaporator residual concentrate can both be determined to develop a material balance from which the final concentration of stabilizer in the evaporator concentrate can be calculated without actually analyzing the concentrate for stabilizer content.

The cloud time is a measure of the polymerization rate of lower molecular weight polyoxymethylenes in the liquid paraformaldehyde. As the molecular weight of polymer builds up in the liquid paraformaldehyde, high polymers become insoluble and begin to precipitate, causing increasing cloudiness in the solution. The length of time required for the solution to become cloudy (cloud time) has been correlated with smoothness of operation in paraformaldehyde manufacture, short cloud times (e.g., about 45 minutes or less) being correlated with heat exchanger fouling and unsatisfactory paraformaldehyde flake quality while long cloud times (approximately 85 minutes or longer) have been correlated with a substantial reduction of apparatus fouling in paraformaldehyde manufacture.

In connection with the cloud time test as described above it will be understood that the concentrated paraformaldehyde solutions with which the presently-described stabilizers are employed must be handled at relatively high temperatures above their normal freezing point, e.g. of the order of about 100° C., in order to remain liquid. Below about 80° to 85° C., depending to some extent on the actual concentration of the material, it will solidify so rapidly that the cloud time becomes meaningless. Also, of course, it becomes relatively meaningless to discuss avoiding solids deposition from a "liquid" which is no longer a liquid. Therefore, it will be understood that the environment in which the stabilizers are used is relatively hot, from at least about 109° C., for 82% paraformaldehyde solution to at least 115° C. for 88% solutions. This also, incidentally, may be one reason why the colloidal stabilizers of the prior art normally used with relatively dilute formaldehyde solutions are not effective in liquid paraformaldehyde systems. Cellulose gums for example, have been seen to drop out of solution themselves, onto the walls of the apparatus in which the solutions are contained, at the elevated temperatures at which the more concentrated paraformaldehyde liquids are processed and handled.

Formalin as normally used in paraformaldehyde manufacture typically contains small amounts of methanol and has a formic acid content in the range of approximately 0.040 to 0.050 wt %. The present stabilizers are effective in converting such formaldehyde solutions to paraformaldehyde with minimal apparatus fouling. Additionally, however, the stabilizers have been found to be effective in the presence of low concentrations, e.g. about 2 ppm to 15 ppm, of amines as well as approximately 1 ppm of sodium hydroxide. These are not necessarily upper limits of contamination by such alkaline materials that can be tolerated in the presence of these stabilizers, but, rather, actual contaminant levels which happen to have been tested with stabilizer efficacy having been observed.

As the terms "formaldehyde concentration" or "paraformaldehyde concentration" are employed herein, it will be understood by those acquainted with the properties of formaldehyde that a better term might be "formaldehyde moiety", since in those solutions the formaldehyde is always present in oligomeric or polymeric form rather than as the monomer.

The following examples are given by way of illustration of the invention. It will be understood that many variations can be made therefrom within the scope of the invention.

EXAMPLE I

Cloud times as defined hereinabove were determined for several compounds which were being investigated as potential stabilizers in paraformaldehyde production. The initial concentration of the formalin used as evaporation feedstock was approximately 51%, and the additive concentrations as listed in the following table are the concentrations in the initial formalin feedstock before it was concentrated in the evaporator. The final additive concentration in the evaporator concentrate was approximately 2 times as high as the initial concentration listed in the table.

TABLE I

COMPOUNDS INVESTIGATED AS POTENTIAL POLYMERIZATION MODERATORS FOR USE IN PARAFORMALDEHYDE PRODUCTION

| Compound | Concentration in Formalin as Fed | Cloud Time | Effect |
| --- | --- | --- | --- |
| Blank | | 45–60 min. | Blank cloud times were run periodically during these tests. |
| Acetic Acid | 38 ppm | 60 min. | No Effect |
| Acetic Acid | 100 ppm | 60 min. | No Effect |

TABLE I-continued
COMPOUNDS INVESTIGATED AS POTENTIAL POLYMERIZATION MODERATORS FOR USE IN PARAFORMALDEHYDE PRODUCTION

| Compound | Concentration in Formalin as Fed | Cloud Time | Effect |
| --- | --- | --- | --- |
| Propionic Acid | 27 ppm | 55 min. | No Effect |
| Propionic Acid | 150 ppm | 55 min. | No Effect |
| Propionic Acid | 300 ppm | 65 min. | No Effect |
| Oxalic Acid | 27 ppm | 15 min. | Detrimental |
| Sebacic Acid | 15 ppm | 20 min. | Detrimental |
| Salicylic Acid | 19 ppm | 20 min. | Detrimental |
| 4-Butyrolactone | 35 ppm | 55 min. | No Effect |
| Phthalic Acid | 8.1 ppm | 5 min. | Detrimental |
| Sodium Salt of Ethylenediaminetetraacetic Acid | 20 ppm | 20 min. | Detrimental |
| Tartaric Acid | 14 ppm | 72 min. | Positive |
| Poly(Acrylic) Acid | 48 ppm | 205 min. | Positive |
| Ethylenediaminetetraacetic Acid | 50 ppm | 95 min. | Positive |
| dl-Malic Acid | 50 ppm | 90 min. | Positive |
| Citric Acid | 50 ppm | 85 min. | Positive |
| Citric Acid | 25 ppm | 85 min. | Positive |
| Citric Acid | 12 ppm | 80 min. | Positive |
| Glycolic Acid | 50 ppm | 55 min. | No Effect |

EXAMPLE II

Citric acid as a polymerization moderator was tested in an operating paraformaldehyde unit comprising two stages of evaporation as described in the two patents to MacLean et al. previously identified hereinabove plus a third stage. The third stage is not always used, but was in this instance. The first stage of evaporation was at about 79.5° C. with the concentrated paraformaldehyde liquid produced in the evaporator containing about 62% paraformaldehyde. The second evaporation stage was at about 93° C. and the evaporator concentrate produced was at 82% paraformaldehyde concentration. In the third stage the temperature and concentrate concentration were about 118° C. and 89% paraformaldehyde concentration, respectively. The pH in concentrated paraformaldehyde solutions has little meaning, but the formic acid concentration in the first stage was about 0.15%, in the second stage about 0.11%, and in the third stage about 0.11%. The heating element in each evaporator was a shell- and tube-heat exchanger heated by steam on the shell side and with rapid recirculation of the liquid which was being evaporated on the tube side. The total liquid being fed into the first evaporation stage, which consisted of a mixture of fresh 51% formaldehyde solution along with internally-generated recycles derived from evaporator distillates which had been further reconcentrated before returning to the first evaporation stage, comprised, in its totality, a 52% solution of formalin containing minor quantities of methanol and formic acid normally present as minor contaminants in formalin solutions. No polymerization moderators were incorporated into the formalin being fed into the first evaporation stage. Operating in this manner, the evaporators typically required cleaning to remove high molecular weight paraformaldehyde solid deposits from the evaporator heating surfaces, especially the second stage evaporator, at intervals of about 17 to 21 days.

With the paraformaldehyde evaporators operating in the same manner described above but with citric acid in a concentration of approximately 10 to 20 ppm being incorporated into the formalin entering the first evaporation stage, the evaporators did not require any shutdown for removing paraformaldehyde deposits for a period of 28 to 38 days.

Although the concentration of citric acid in the second-stage evaporator concentrate was not measured directly, it was calculated, from a material balance of the evaporator system, to be approximately 20 to 40 ppm. In the third stage it was approximately 22 to 40 ppm.

It will be noted that the operating temperature in the second-stage evaporator as given above (93° C.) is slightly lower than the temperature of about 109° C. set forth earlier hereinabove as the approximate lower limit of temperature needed to handle 82% paraformaldehyde. The 93° C. was actually read from the instruments associated with the evaporator and may reflect the fact that, in what amounts to a flowing system, the polymerization reactions were not being given time to reach completion. The temperature of 139° C. represents laboratory test data based on static tests in which a longer time was allowed during which more extensive polymerization occurred.

The embodiments of the invention in which an exclusive property or privilege is claimed are defined as follows:

1. An aqueous formaldehyde composition characterized by resistance to the deposition of long-chain paraformaldehyde solids therefrom when it is concentrated to a liquid paraformaldehyde containing at least about 80 wt % formaldehyde moiety, which composition consists essentially of water, formaldehyde, and a polymerization moderator selected from the group consisting of polyacrylic acid, tartaric acid, dl-malic acid, ethylenediaminetetraacetic acid, and citric acid.

2. The composition of claim 1 wherein said composition contains about 50% formaldehyde, 50% water, and about 10 ppm to 50 ppm of said moderator.

3. An aqueous formaldehyde composition which is resistant to the deposition of long-chain solid paraformaldehyde polymers therefrom at temperatures above its normal freezing point, which composition comprises at least about 80% formaldehyde moiety, an effective amount of a polymerization moderator selected from the group consisting of polyacrylic acid, tartaric acid, dl-malic acid, ethylenediaminetetraacetic acid, and citric acid; and the remainder water.

4. In a process for producing a liquid paraformaldehyde which comprises subjecting a formalin feedstock to vacuum evaporation to produce a liquid paraformaldehyde evaporator concentrate containing at least about 80% formaldehyde moiety, the improvement which comprises:

reducing the tendency of said evaporator concentrate to deposit solid paraformaldehyde polymers on the surfaces of the evaporation apparatus which are in contact with said concentrate by maintaining within the formalin which is being subjected to said vacuum evaporation an effective amount of a polymerization moderator selected from the group consisting of polyacrylic acid, tartaric acid, dl-malic acid, ethylenediaminetetraacetic acid, and citric acid.

5. The improvement of claim 4 wherein the polymerization moderator is citric acid.

* * * * *

UNITED STATES PATENT AND TRADEMARK OFFICE
CERTIFICATE OF CORRECTION

PATENT NO. : 4,289,912
DATED : September 15, 1981
INVENTOR(S) : Marvin E. Harris, Jr.; Hubert H. Thigpen It is certified that error appears in the above-identified patent and that said Letters Patent are hereby corrected as shown below:

In column 1, line 29, after "which the," insert --present invention is concerned, is described in--.

Signed and Sealed this

First Day of December 1981

[SEAL]

Attest:

GERALD J. MOSSINGHOFF

*Attesting Officer* *Commissioner of Patents and Trademarks*